(12) United States Patent
Durst et al.

(10) Patent No.: US 9,024,268 B2
(45) Date of Patent: May 5, 2015

(54) ONE-DIMENSIONAL X-RAY DETECTOR WITH CURVED READOUT STRIPS

(71) Applicant: Bruker AXS, Inc., Madison, WI (US)

(72) Inventors: Roger D. Durst, Middleton, WI (US); Peter Laggner, Graz (AT); Sergei A. Medved, Madison, WI (US); Bruce L. Becker, Madison, WI (US)

(73) Assignee: Bruker AXS, Inc., Madison, WI (US)

( * ) Notice: Subject to any disclaimer, the term of this patent is extended or adjusted under 35 U.S.C. 154(b) by 5 days.

(21) Appl. No.: 13/833,346

(22) Filed: Mar. 15, 2013

(65) Prior Publication Data

US 2014/0264046 A1  Sep. 18, 2014

(51) Int. Cl.
*G01T 1/24* (2006.01)
*G01T 1/16* (2006.01)
*G01N 23/201* (2006.01)

(52) U.S. Cl.
CPC ............ *G01T 1/1606* (2013.01); *G01T 1/24* (2013.01); *G01N 23/201* (2013.01); *G01N 2223/054* (2013.01)

(58) Field of Classification Search
USPC .................................................. 250/370.01
See application file for complete search history.

(56) References Cited

U.S. PATENT DOCUMENTS

| | | | |
|---|---|---|---|
| 6,751,288 B1 | 6/2004 | Hessler | |
| 7,406,153 B2 * | 7/2008 | Berman | 378/86 |
| 2002/0053641 A1 * | 5/2002 | Verbruggen | 250/370.09 |
| 2006/0083350 A1 * | 4/2006 | Gerndt et al. | 378/70 |
| 2006/0269045 A1 * | 11/2006 | Jiang | 378/88 |
| 2008/0069302 A1 * | 3/2008 | Jiang | 378/86 |
| 2009/0067573 A1 | 3/2009 | Yokhin et al. | |
| 2010/0284516 A1 * | 11/2010 | Jiang | 378/86 |
| 2013/0329858 A1 * | 12/2013 | Jiang | 378/87 |
| 2013/0329861 A1 * | 12/2013 | Jiang et al. | 378/148 |

FOREIGN PATENT DOCUMENTS

EP  1647840 A2  4/2006

OTHER PUBLICATIONS

Author: Igor Petrovich Dolbnya, Title: A Synchrotron Small-Angle X-ray Scattering Study of Order/Disorder in Colloidal Crystals, Date: Mar. 2004, Publisher: ISBN 90-393-3649-0.*

(Continued)

*Primary Examiner* — David J Makiya
*Assistant Examiner* — Taeho Jo
(74) *Attorney, Agent, or Firm* — Robic, LLP

(57) ABSTRACT

A detector for a small-angle x-ray diffraction system uses curved readout strips shaped to correspond to the expected intensity distribution of x-rays scattered by the system. This expected intensity distribution may be a series of concentric circles, and each of the strips has a shape that approximates a section of an annulus. The strips may be positioned on a substrate such that a center of curvature of the curved strips is located along an edge of a readout region within which the strips are located or, alternatively, at a geometric center of the readout region. The detector may have a signal readout system that uses a delay line or, alternatively, a multichannel readout system. The detector may make use of electron generation via interaction of the diffracted x-ray beam with a gas in a gas chamber, or through interaction of the diffracted beam with a semiconductor material.

20 Claims, 3 Drawing Sheets

(56) References Cited

OTHER PUBLICATIONS

Author: Cabal et al., Title: Feasibility of Silicon strip detectors and low noise multichannel readout system for medical digital radiography, Date: 2002, Publisher: CP630, Medical Physics, Sixth Mexican Symposium, edited by L. M. Montano Zetina and G. Herrera Corral © 2002 American Institute of Physics.*

Author: Bob B. He, Title: Two-Dimensional X-Ray Diffraction, Date: 2009, Publisher: John Wiley & Sons, Inc., Hoboken, New Jersey.*

Author: Dolbnya et al., Title: A fast position sensitive microstrip-gas-chamber detector at high count rate operation, Date: Nov. 2002, Publisher: American Institute of Physics.*

Author: M.H.J. Koch, Title: SAXS Instrumentation for Synchrotron Radiation then and now, Date: 2010, Publisher: IOP, XIV International Conference on Small-Angle Scattering (SAS09), Journal of Physics: Conference Series 247 (2010) 012001.*

De Lurgio P M et al: "A new detector for Time-Resolved Small-Angle X-Ray Scattering Studies", Nuclear Science Symposium Conference Record, 2005 IEEE Wyndham El Conquistador Resort, Puerto-Rico Oct. 23-29, 2005, Piscataway, NJ, USA, IEEE, vol. 2, Oct. 23-29, 2005 (Oct. 23, 2005), pp. 1215-1222, XP010895773, ISBN: 978-0-7803-9221-2, Paragraph II.

S K Kiprich et al: "Very low mass microcables for the ALICE silicon strip detector", Jan. 1, 1999, retrieved from the internet : http://dx.doi.org/10.5170/CERN-1999-009.143, Paragraph 1.

Duval B P et al: "Windowless position-sensitive X-Ray detector for a rowland circle crystal spectrometer", Review of Scientific Instruments, AIP, Melville, NY, US, vol. 57, No. 8, part 2, Aug. 1, 1986, pp. 2156-2158, p. 2156, right-hand column.

A.R. Forouhi et al: "Small-angle x-ray scattering system with linear position-sensitive detector", IEEE Symposium on Nuclear Science, San Francisco, CA, Apr. 1, 1981, retrieved from the internet : http://escholarship.org/uc/item/92h5t19w.pdf.

* cited by examiner

ONE-DIMENSIONAL X-RAY DETECTOR WITH CURVED READOUT STRIPS

BACKGROUND OF THE INVENTION

1. Field of the Invention

This invention relates generally to the field of x-ray diffraction and, more particularly, to x-ray detectors that use readout strips for the detection of electrons generated by incoming x-ray energy.

2. Description of the Related Art

In the field of x-ray diffraction, particularly small-angle x-ray scattering (SAXS), a sample is subjected an incident x-ray beam, and a low-angle x-ray diffraction signal from the sample is recorded with a detector. A typical SAXS configuration, known as a Kratky camera, is shown schematically in FIG. 1. In this configuration, an x-ray beam 10 from an x-ray source (not shown) is directed toward offset blocks 12 and 14 that, together, make up a Kratky collimator. The Kratky collimator shapes the beam to a ribbon-like profile, having a long, thin cross section. Due to the arrangement of the blocks 12, 14, there is very little scattering of the x-ray beam, and thus minimal background noise, to the side of the beam on which the block 14 is located. In the path of the collimated beam is located a sample 16 that, in this example, is a liquid in a capillary tube. Small-angle scatter from the sample 16 is then collected by a detector 18, which may be either a one-dimensional or a two-dimensional detector. As shown in the figure, the detector is positioned such that the distribution of the diffraction signal is centered along the edge of the detector, so that the detection surface resides in the region of minimal x-ray scatter (i.e., to the same side of the beam as collimator block 14). As such, only a portion (typically half) of the diffraction signal from the sample 16 is collected.

Because the distribution of x-rays is isotropic, a one-dimensional detector is often used to record the scattered radial x-ray profile. One-dimensional detectors (also known as linear or "strip" detectors) have the advantage of being simpler, less expensive and less complex than two-dimensional detectors. One type of linear detector makes use of a series of straight readout strips as shown schematically in the example of FIG. 2. The detector 20 may be based on a gas electron multiplier, or it may be a semiconductor detector, and it includes readout strips 22 that run parallel to one another, covering an area upon which the diffraction signal is incident (indicated at 24 in the figure). The strips may consist of, for example, silicon diodes in a semiconductor strip detector, or metallic strips in a gaseous detector.

In the example of FIG. 2, each of the readout strips detects photoelectrons generated from the interaction of the x-ray energy with a gas or a semiconductor material. There is no spatial discrimination in a direction parallel to the strips, and the accumulated electron signal for the entire strip must be read out together. Typically, the readout strips are connected to a delay line that is, in turn, connected to a time-to-digital converter to record the x-ray positional data. Alternatively, each strip may be connected a preamplifier which is connected to multichannel readout electronics.

SUMMARY OF THE INVENTION

In accordance with the present invention, a detector is provided for detecting a diffracted x-ray beam from a small-angle x-ray diffraction system. The detector makes use of readout strips at which electrons generated by the energy of the diffracted x-ray beam are collected. The readout strips each follow a different curved path that corresponds to a region of substantially constant intensity of the x-ray beam, and are each located adjacent to one another in a readout plane. A signal readout system detects the presence of electrical signals at the readout strips that result from the collected electrons, and associates each electrical signal with the readout strip at which it originated.

The generation of electrons from the diffracted x-ray beam may be done in different ways. For example, the detector may have a gas chamber in which the diffracted x-ray beam interacts with gas molecules to generate the electrons, which are collected by metallic readout strips. It is also possible that the readout strips include a semiconductor material within which the electrons are generated by direct interaction with the diffracted x-ray beam.

The shape of the readout strips is based on the expected distribution of the diffracted x-rays. In one embodiment, each of the readout strips has a shape that approximates a section of an annulus. More particularly, the readout strips may comprise adjacent annular segments whose respective curvatures correspond to a set of concentric circles in the readout plane. The readout strips, taken together, form a readout zone on the substrate within which the electrons are collected. In one embodiment of the invention, the concentric circles followed by the readout strips are centered about a point that is along the edge of the readout zone. This may correspond to an arrangement in which the diffracted x-ray signal originates from a sample illuminated by an incident x-ray beam from a Kratky camera. In another embodiment, the readout strips may be arranged such that the concentric circles are centered about a point substantially at the center of the readout zone. This may correspond to an arrangement in which the diffracted x-ray beam originates from a sample illuminated by an incident x-ray beam from a three pinhole camera.

The signal readout system of the present invention may also take different forms. In an exemplary embodiment, the system comprises a delay line that is connected individually to each of the readout strips. Impedance elements may be distributed along the delay line, each being located between two connection points between the delay line and the readout strips. In another embodiment, the readout system is a multichannel readout system to which each readout strip has an independent input.

DETAILED DESCRIPTION

Figure 1:
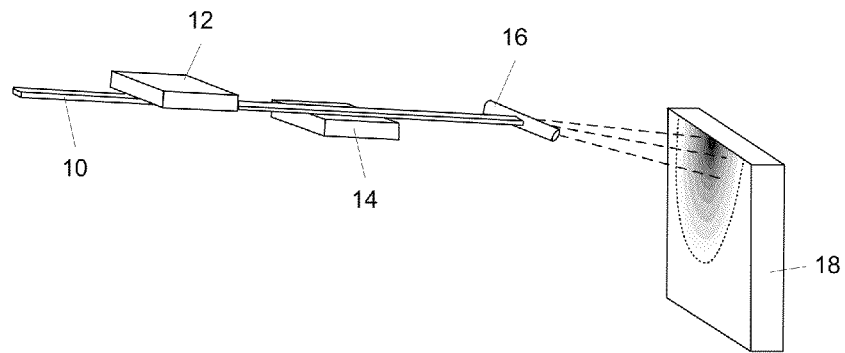
FIG. 1 is a schematic view of a small-angle x-ray diffraction system using a Kratky camera, as is known in the art.
Figure 2:
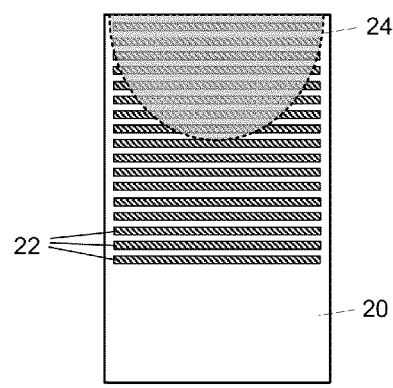
FIG. 2 is a schematic view of the readout strips of a detector from a prior art small-angle x-ray diffraction system.
Figure 3:
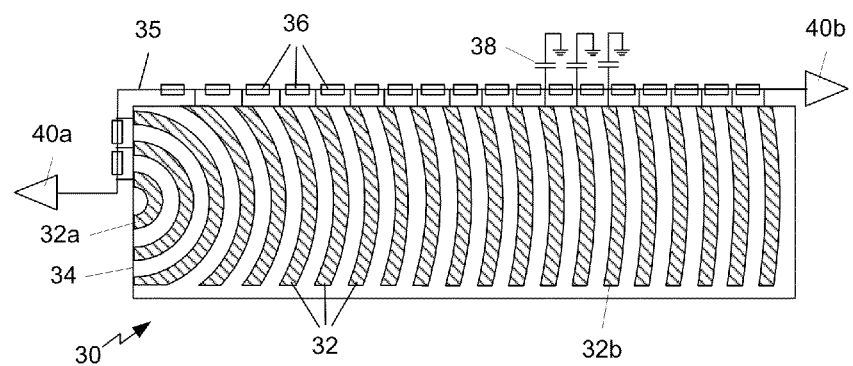
FIG. 3 is a schematic view of the readout strips of a detector from a small-angle x-ray diffraction system according to an embodiment of the invention for which a delay line readout system is used.

Shown in FIG. 3 is a schematic view of a one-dimensional x-ray detector 30 according to the present invention. The detector 30 is arranged to receive an isotropic x-ray distribution that is centered along a first edge 34 of the detector. The intensity of the x-ray energy in the detected signal varies in a radial direction, the overall signal being circularly symmetric about the center. Thus, the intensity distribution of the diffracted x-ray signal may be viewed as concentric diffraction rings (sometimes referred to as "Debye" rings) of relatively constant intensity surrounding the expected center.

To detect the x-ray signal, the detector 30 uses a series of readout strips 32 that are each connected to a delay line 35. The readout strips 32 may be metallic, if used in conjunction with a gaseous detector, or they may be of a semiconductor material, with which the x-ray signal interacts directly. As shown in the figure, the readout strips are curved, each roughly following a line of expected constant intensity of the diffracted signal. Thus, since the signal is centered along the edge 34 of the detector, the curvature of the readout strip 32a is more pronounced than that of strip 32b, which is much further from the center than strip 32a. However, those skilled in the art will recognize that, although the strips 32 are only partial rings, they each follow a path having a constant distance from the expected center of the x-ray signal distribution.

Because the shape of the readout strips follows the different intensity rings of the x-ray diffraction signal, each readout strip detects signal energy from only one radial position relative to the expected center of the diffraction signal. That is, x-ray signal energy from one radial position in the signal distribution does not cross multiple readout strips, as would be the case if the strips followed a straight line. In such a case, the straight line strips would detect signal energy from different intensity rings of the x-ray distribution, leading to a smearing of the detected signal. Using the curved strips of the present invention, however, such smearing effects are avoided.

In the embodiment of FIG. 3, the delay line 35 allows for determination of the intensity detected at each of the readout strips 32. As shown, each of the strips has a connection to the delay line, and adjacent connection points are separated by an inductive element 36 that, together with a capacitance to ground, provides a desired impedance between the respective readout strips 32. Several examples of this capacitance are shown in the figure and those skilled in the art will understand that a similar capacitive ground connection is provided for each of the readout strips 32. Thus, in this embodiment, the delay line is an LC lumped parameter delay line. At each end of the delay line 35 is a preamplifier 40a, 40b that provides amplification to a signal detected at one of the readout strips. The outputs from preamplifiers 40a, 40b may then be compared to determine at which readout strip the signal was received, since the relative delay between the appearance of the signal at each of the preamplifiers indicates the location of the detected signal relative to the delay line. In this way, the intensity and position of the diffracted x-ray signal relative to the readout strips may be determined.

Because of the curved shape of the readout strips, the capacitance value is not constant from one strip to the next, as it would be if all of the strips were straight and parallel. Because of this, the propagation of signals in the delay line configuration shown in FIG. 3 will not be constant. This effect can be compensated for by appropriate selection of the delay line capacitance. For example, in a lumped parameter delay line, the lumped capacitance in each delay element (that is, between two adjacent strips) is decreased as the strip length increases such that the total capacitance is constant. This can be accomplished by adjusting the values of either the inductance, the capacitance or both. Those skilled in the art will also recognize that there are also other options for implementing the delay line, including the use of a serpentine-type delay line in which the delay is generated by a conducting path which meanders between each strip in order to produce the appropriate signal delay.

Figure 4:
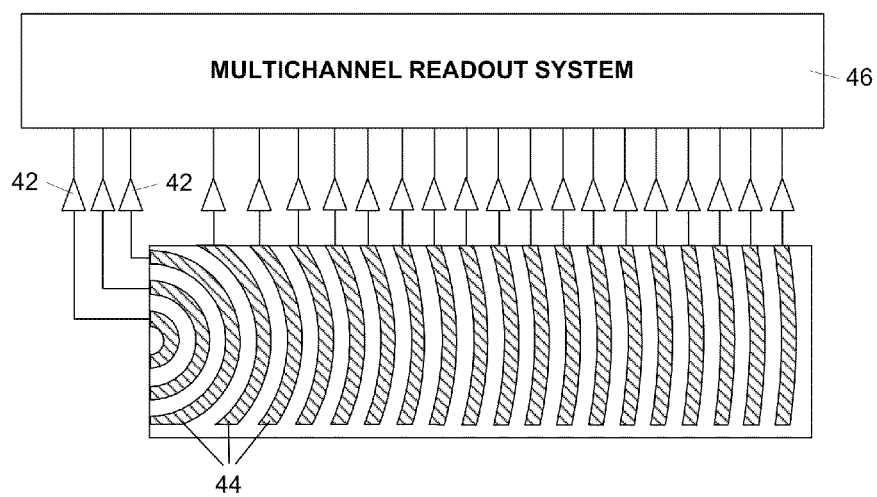
FIG. 4 is a schematic view of the readout strips of a detector from a small-angle x-ray diffraction system according to an embodiment of the invention for which a multichannel readout system is used.

Another way to avoid the effect of the variable strip capacitance is to connect each strip to a readout preamplifier and then to a multichannel readout system, as is shown schematically in FIG. 4. In this embodiment, a separate preamplifier 42 is provided for each readout strip 44, and the output of each preamplifier is detected and recorded by multichannel readout system 46. Thus, unlike the delay line embodiment, the embodiment of FIG. 4 provides independent monitoring of each readout strip 44. In addition, by using a multichannel readout system, all of the readout strips may be detected simultaneously, allowing a much faster detection cycle. However, this embodiment is also more complex and costly to fabricate than the delay line embodiment of FIG. 3.

As mentioned above, the focusing of the x-ray distribution along an edge of the detector sacrifices half of the viewing angle, but avoids the x-ray energy scattered from the collimator, which would otherwise greatly reduce the signal-to-noise ratio. However, for other system arrangements, it may be possible to use all of the diffracted x-ray energy in an efficient manner. A detector for use in such a situation is shown schematically in FIG. 5.

Figure 5:
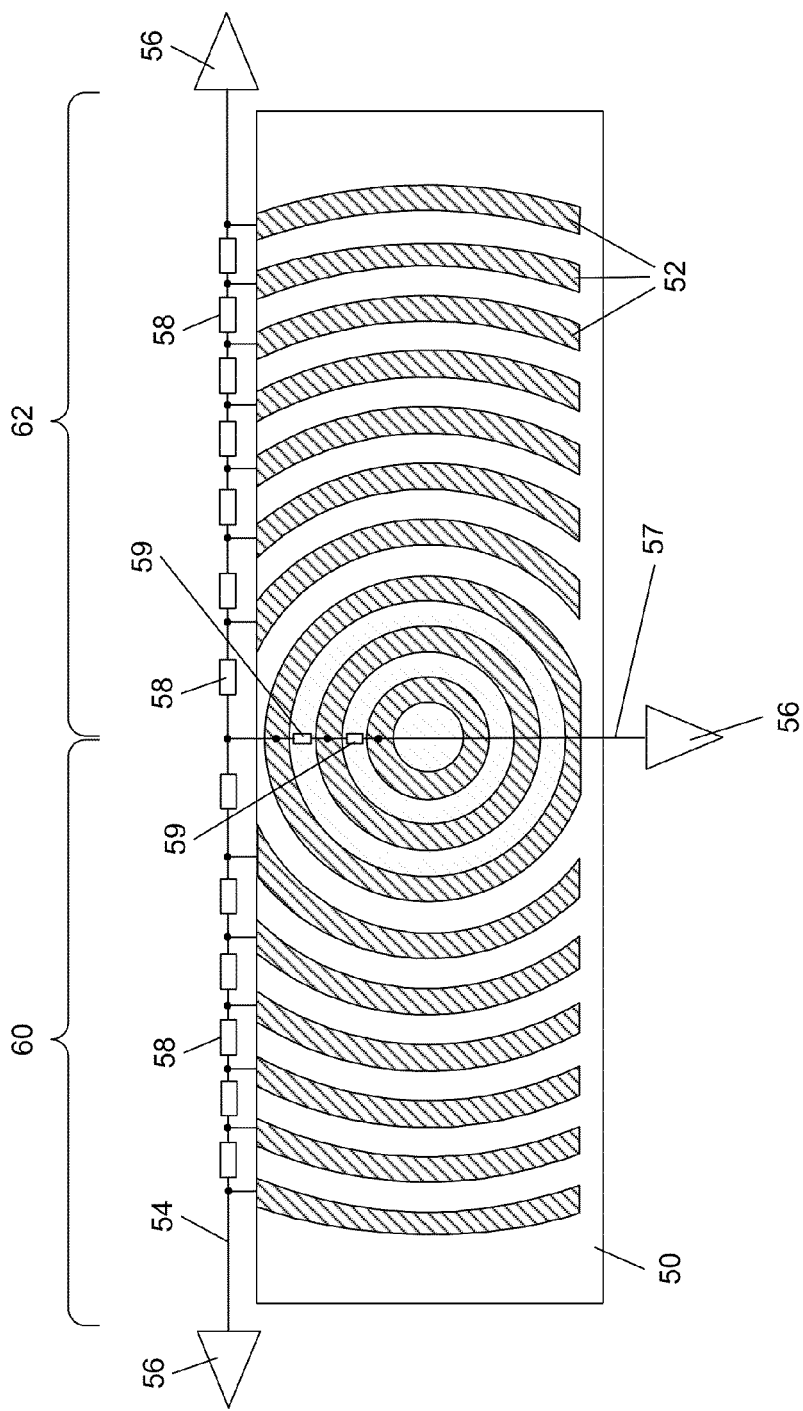
FIG. 5 is a schematic view of the readout strips of a detector from a small-angle x-ray diffraction system according to an embodiment of the invention for which the readout strips follow a set of concentric circles that are centered about a center point of a substrate on which the readout strips are located.

The embodiment of FIG. 5 is similar to that of FIG. 4, except that the curved readout strips of the detector are centered about a point near the middle of the detector, rather than along its edge. This alternative embodiment may be more suitable for a camera based on a three pinhole geometry. In such a camera arrangement, known in the art, an incident x-ray beam is passed through three consecutive pinholes. The beam has a width and an angular divergence, and the first two pinholes are used to form a desired beam. The formed beam then passes through the third pinhole, while x-ray energy scattered by the second pinhole is blocked by the opaque material in which the third pinhole is formed.

Because the arrangement of FIG. 5 does not have a high amount of scattered x-ray radiation to one side of the camera (as in the case of a Kratky camera), the diffracted x-ray signal may be centered on the center of the detector 50. Each curved readout strip 52, as in the embodiments of FIGS. 3 and 4, follows an arc that makes up at least part of a circle that is concentric with circles followed by the other strips. Thus, the readout strips follow the curved lines of x-ray intensity expected in the diffracted x-ray signal, and are subjected to a minimal amount of noise from scatter.

As in the FIG. 3 embodiment, the detector of FIG. 5 uses a delay line 54 with a preamplifier 56 at each end. The impedance elements separating the connections of the readout strips to the delay line include impedance elements 59 connected to the innermost readout strips, for which an entire circular path fits within the detector profile. These impedance elements 59 are connected to an additional branch 57 of the delay line 35, which terminates in a third preamplifier 56. If the portion of the delay line 54 containing the impedance elements 58 is viewed as two branches 60, 62 that are separated by the point of contact with branch 57, the three branches 60, 62, 57 should be configured using impedance matching techniques. Those skilled in the art will also recognize that the configuration shown in FIG. 5 may also be applied to a multichannel readout arrangement such as that of the FIG. 4 embodiment, in which each readout strip is connected directly to a preamplifier and is detected independently of the other strips.

While the invention is shown and described with reference to a preferred embodiment thereof, those skilled in the art will recognize that various changes in form and detail may be made herein without departing from the spirit and scope of the invention as defined by the appended claims.

What is claimed is:

1. A detector for detecting a diffracted x-ray beam from a small-angle x-ray diffraction system, the detector comprising:
   a plurality of readout strips on a substantially planar substrate at which electrons generated by the energy of the diffracted x-ray beam are collected, the readout strips each following a different curved path that corresponds to a region of substantially constant intensity of the diffracted x-ray beam, and each being located adjacent to one another within a readout plane; and
   a signal readout system that detects the presence of electrical signals at the readout strips resulting from said collected electrons and associates each electrical signal with the readout strip at which it originated.

2. A detector according to claim 1 wherein the detector comprises a gas chamber in which said electrons are generated.

3. A detector according to claim 1 wherein the detector comprises a semiconductor material within which said electrons are generated.

4. A detector according to claim 1, wherein the readout strips each have a shape that approximates a section of an annulus.

5. A detector according to claim 1 wherein the readout strips comprise adjacent annular segments whose respective curvatures correspond to a set of concentric circles in the readout plane.

6. A detector according to claim 5 wherein the readout strips together form a readout zone within which said electrons are collected, and wherein said concentric circles are centered about a point substantially at an edge of the readout zone.

7. A detector according to claim 6 wherein the diffracted x-ray beam originates from a sample illuminated by an incident x-ray beam from a Kratky camera.

8. A detector according to claim 5 wherein the readout strips together form a readout zone on the substrate within which said electrons are collected, and wherein said concentric circles are centered about a point substantially at a center of the readout zone.

9. A detector according to claim 8 wherein the diffracted x-ray beam originates from a sample illuminated by an incident x-ray beam from a three pinhole camera.

10. A detector according to claim 1 wherein the signal readout system comprises a multichannel readout system to which each readout strip has an independent input.

11. A detector according to claim 1 wherein the signal readout system comprises a delay line.

12. A detector according to claim 11 wherein the delay line is connected individually to each of the readout strips, and wherein impedance elements are distributed along the delay line, each being located between two connection points connecting adjacent readout strips, respectively, to the delay line.

13. A detector for detecting a diffracted x-ray beam from a small-angle x-ray diffraction system, the detector comprising:
    a plurality of readout strips on a substantially planar substrate at which electrons generated by the energy of the diffracted x-ray beam are collected, the readout strips each having a shape that approximates a section of an annulus and being located adjacent to one another within a readout plane such that the shape of each of the strips follows a different one of a set of concentric circles within said plane; and
    a signal readout system that detects the presence of electrical signals resulting from said collected electrons and associates each electrical signal with the readout strip at which it originated.

14. A method of producing a detector for detecting a diffracted x-ray beam from a small-angle x-ray diffraction system, the method comprising:
    providing a substantially planar substrate material;
    determining an anticipated form of an x-ray distribution of said diffracted x-ray beam at a readout plane, said distribution including different contours of substantially constant intensity;
    depositing on the substrate material a plurality of readout strips at which electrons generated by the energy of the diffracted x-ray beam are collected, each of the readout strips having a curved shape that corresponds to one of said contours; and
    connecting each of the readout strips to a signal readout system that detects electrical signals resulting from said collected electrons and associates each electrical signal with the readout strip at which it originated.

15. A method according to claim 14 further comprising providing, adjacent to the substrate, a gas chamber in which said electrons are generated.

16. A method according to claim 14 wherein the readout strips each have the shape of a section of an annulus.

17. A method according to claim 14 wherein the readout strips comprise adjacent annular segments whose respective curvatures correspond to a set of concentric circles in the plane of the substrate.

18. A method according to claim 17 wherein the readout strips together form a readout zone on the substrate within which said electrons are collected, and wherein said concentric circles are centered about a point at the edge of the readout zone.

19. A method according to claim 17 wherein the readout strips together form a readout zone on the substrate within which said electrons are collected, and wherein said concentric circles are centered about a point near a center of the readout zone.

20. A method according to claim 14 wherein the signal readout system comprises a delay line.

* * * * *